US012016602B2

(12) United States Patent
Schaefer et al.

(10) Patent No.: US 12,016,602 B2
(45) Date of Patent: Jun. 25, 2024

(54) MIS BUNION CORRECTION SYSTEM

(71) Applicants: Brett J. Schaefer, Tinley Park, IL (US); Thomas Zink, San Antonio, TX (US); David Alan Yeager, Dixon, IL (US)

(72) Inventors: Brett J. Schaefer, Tinley Park, IL (US); Thomas Zink, San Antonio, TX (US); David Alan Yeager, Dixon, IL (US)

(*) Notice: Subject to any disclaimer, the term of this patent is extended or adjusted under 35 U.S.C. 154(b) by 120 days.

(21) Appl. No.: 17/672,821

(22) Filed: Feb. 16, 2022

(65) Prior Publication Data

US 2022/0273348 A1  Sep. 1, 2022

Related U.S. Application Data

(60) Provisional application No. 63/154,065, filed on Feb. 26, 2021.

(51) Int. Cl.
*A61B 17/80* (2006.01)
*A61B 17/17* (2006.01)
(Continued)

(52) U.S. Cl.
CPC ...... *A61B 17/8061* (2013.01); *A61B 17/8057* (2013.01); *A61B 17/86* (2013.01); *A61B 2017/00831* (2013.01); *A61B 2017/00982* (2013.01); *A61B 17/151* (2013.01); *A61B 17/1728* (2013.01); *A61B 17/1775* (2016.11); *A61B 2017/564* (2013.01); *A61B 2017/565* (2013.01); *A61B 2017/681* (2013.01); *A61B 17/8615* (2013.01);
(Continued)

(58) Field of Classification Search
CPC .... A61F 2002/30578; A61F 2002/4233; A61F 2002/4228; A61F 2/4225; A61B 2017/681; A61B 2017/564; A61B 2017/565; A61B 17/8061; A61B 17/8057; A61B 17/861; A61B 17/8615; A61B 17/863; A61B 17/1728; A61B 17/151; A61B 17/152; A61B 17/1775
USPC ......................................................... 606/282
See application file for complete search history.

(56) References Cited

U.S. PATENT DOCUMENTS

2003/0060827 A1* 3/2003 CoughIn ............ A61B 17/8061
606/70
2006/0015102 A1* 1/2006 Toullec .............. A61B 17/8095
606/281

(Continued)

*Primary Examiner* — Marcela I. Shirsat
(74) *Attorney, Agent, or Firm* — Brennan, Manna & Diamond, LLC

(57) ABSTRACT

A bunion correction device is disclosed which secures a plate to a metatarsal head before an osteotomy is performed to allow for control of the metatarsal head during the bunion correction procedure. The device comprises a body component having two opposing portions positioned orthogonally to one another with a plurality of screw apertures positioned on both portions of the implant. Bone screws or fasteners are driven laterally through the apertures of the first portion into the metatarsal head, securing the first portion or base to the metatarsal head. An osteotomy is performed just proximal to the plate and the metatarsal head is translated to correct the bunion. Bone screws are then placed in the second portion apertures to fix the correction and provide compression of the osteotomy.

13 Claims, 5 Drawing Sheets

(51) Int. Cl.
*A61B 17/56* (2006.01)
*A61B 17/86* (2006.01)
*A61F 2/42* (2006.01)
A61B 17/00 (2006.01)
A61B 17/15 (2006.01)
A61B 17/68 (2006.01)
A61F 2/30 (2006.01)

(52) U.S. Cl.
CPC ... *A61F 2002/30578* (2013.01); *A61F 2/4225* (2013.01); *A61F 2002/4228* (2013.01); *A61F 2002/4233* (2013.01)

(56) References Cited

U.S. PATENT DOCUMENTS

| | | | | |
|---|---|---|---|---|
| 2011/0306977 | A1* | 12/2011 | Michel | A61B 17/8014 606/281 |
| 2014/0066995 | A1* | 3/2014 | McCormick | A61B 17/8052 606/280 |
| 2015/0272642 | A1* | 10/2015 | Leemrijse | A61B 17/8061 606/291 |
| 2017/0020569 | A1* | 1/2017 | Grant | A61B 17/8057 |

* cited by examiner

MIS BUNION CORRECTION SYSTEM

CROSS-REFERENCE TO RELATED APPLICATION

The present application claims priority to, and the benefit of, U.S. Provisional Application No. 63/154,065, which was filed on Feb. 26, 2021 and is incorporated herein by reference in its entirety.

FIELD OF THE INVENTION

The present invention relates generally to a medical device for use in the field of podiatry. More particularly, the present invention relates to a plate having an adjacent wing or extension forming a generally L-shaped plate device which secures to the metatarsal head before an osteotomy is performed to allow for rotational control and easier correction. Once secured to the metatarsal head, the plate provides for control and placement of the metatarsal head in the corrected construct after performance of an osteotomy. Accordingly, the present disclosure makes specific reference thereto. Nonetheless, it is to be appreciated that aspects of the present invention are also equally applicable to other like applications, devices and methods of manufacture.

BACKGROUND

A bunion (hallux valgus) is a multi-planar angular deformity of the first metatarsophalangeal (MTP) joint. The deformity often causes abnormal fitting of shoes, and causes irritation of the patient's skin in places where the foot rubs against the footwear, which often leads to inflammation and pain. A bunion is caused by a malalignment of the first metatarsal and the proximal phalanx of the hallux. The formation of a bunion alters the distribution of ground reactive forces throughout the human gait cycle, which can also lead to irritation, calluses, blistering and ulceration of the skin, in addition to making walking difficult.

Typically, in order to correct a bunion deformity, an osteotomy is made in the metatarsal which allows the head of the metatarsal to be translated laterally in the transverse plane, which realigns the MTP joint. The osteotomy is then fixated with cortical compression screws or other fasteners. Specifically, an incision is made at the dorsal joint surface. The residual cartilage is then removed from the metatarsal head and phalangeal base. The surgeon will typically create a "ball and socket" configuration of the surfaces using a variety of instrumentation. With the joint surfaces prepared and positioned appropriately, one or more compression screws or other fasteners are placed across the joint and the dorsal plate is positioned and then applied for the corrective action. After implantation of the hardware and fastening the plate in the desired position, the surgical site is closed with retained sutures. The foot and lower leg are then typically placed into a splint until healing occurs.

While traditional methods of correcting bunions are effective, the methods all provide for performing the osteotomy first and then placing the dorsal plate or other implant on the metatarsal shaft before being attached to the metatarsal head. However, there are identifiable shortcomings when this type of correction is utilized. For example, once the osteotomy is complete, the surgeon can lose control of the metatarsal head as nothing is securing the head in place after the osteotomy. This creates difficulty in properly positioning the metatarsal head, especially during an MIS procedure, as proper positioning of the metatarsal head in the sagittal and coronal planes is critical to the bunion correction procedure.

Therefore, there exists a long felt need in the art for an improved medical device for correcting a bunion deformity that allows for enhanced control and placement of the metatarsal head in the corrected construct. The present invention discloses a plate having a wing or other extension resembling an L-shaped plate device which secures to the metatarsal head before the osteotomy is performed to allow for greater surgeon control during the process of the metatarsal head during the bunion correction procedure. Further, the plate with its extension has a plate with a portion extending generally perpendicularly from the plate creating a generally L-shaped body. The body of the invention has two opposing components positioned orthogonally together or in an approximately 85 to about 95 degrees with a 90 degree angle being preferred with a plurality of apertures for insertion of screws or other fasteners on both opposing components of the implant. Bone screws or fasteners are then driven laterally through the apertures of the first opposing component into the metatarsal head. This secures the device to the metatarsal head. Therefore, the plate, which is secured to the metatarsal head before an osteotomy is performed, allows for rotational control and easier correction and adjustment. Additionally, once secured to the metatarsal head, the plate and its extensions provide for control and placement of the metatarsal head in the corrected construct after performance of an osteotomy.

SUMMARY OF THE INVENTION

The following presents a simplified summary in order to provide a basic understanding of some aspects of the disclosed innovation. This summary is not an extensive overview, and it is not intended to identify key or critical elements or to delineate the scope thereof. Its sole purpose is to present some concepts in a simplified form as a prelude to the more detailed description that is presented later.

The subject matter disclosed and claimed herein, in one aspect thereof, comprises a base plate having a supplemental portion extending generally orthogonally or perpendicularly from the base plate that can be secured to the metatarsal head and that allows the surgeon to control the metatarsal head while performing an osteotomy and bunion correction procedure. The base plate of the present invention may be used with open or MIS procedures, and includes a shaped body component having first and second opposing components positioned orthogonally to one another, or in an angle ranging from about 85 to 95 degrees and preferably approximately 90 degree angle. Each of the first and the second opposing components have a plurality of apertures or openings which accept screws or other fasteners for securing the base plate in position. Bone screws or other fasteners are then driven laterally through the apertures or openings of the first opposing component into the metatarsal head. This secures the invention to the metatarsal head.

In a preferred embodiment, the first opposing component of the base plate has two apertures set apart from one another to allow for more bone area to be contacted between the screws. Bone screws or other fasteners are then driven laterally through the apertures or openings to secure the first opposing component to the metatarsal head. The second opposing component of the extension of the plate device has two apertures or openings set in alignment with one another because there is no cortical bone to engage, and to reduce and hopefully avoid the risk of fracturing. The bone screws or fasteners are driven through the apertures at different angles down the metatarsal shaft to fix the correction, and provide compression of the osteotomy.

In another embodiment, the plate further includes a set of guide components which are secured to the two apertures of the second opposing component via threading into the apertures or openings. The guide components are used to control the metatarsal head, control rotation and allow for easier correction and positioning. The guide components can also be used to place pins for temporary fixation.

In another embodiment, the plate with its extension is manufactured as an additively printed titanium component. Nonetheless, the plate and its extension can also be manufactured as a machined titanium component. Additionally, the plate can be manufactured of PEEK, stainless steel, or any other biocompatible material as is known in the art.

To the accomplishment of the foregoing and related ends, certain illustrative aspects of the disclosed innovation are described herein in connection with the following description and the annexed drawings. These aspects are indicative, however of but a few of the various ways in which the principles disclosed herein can be employed and is intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION

Figure 1:
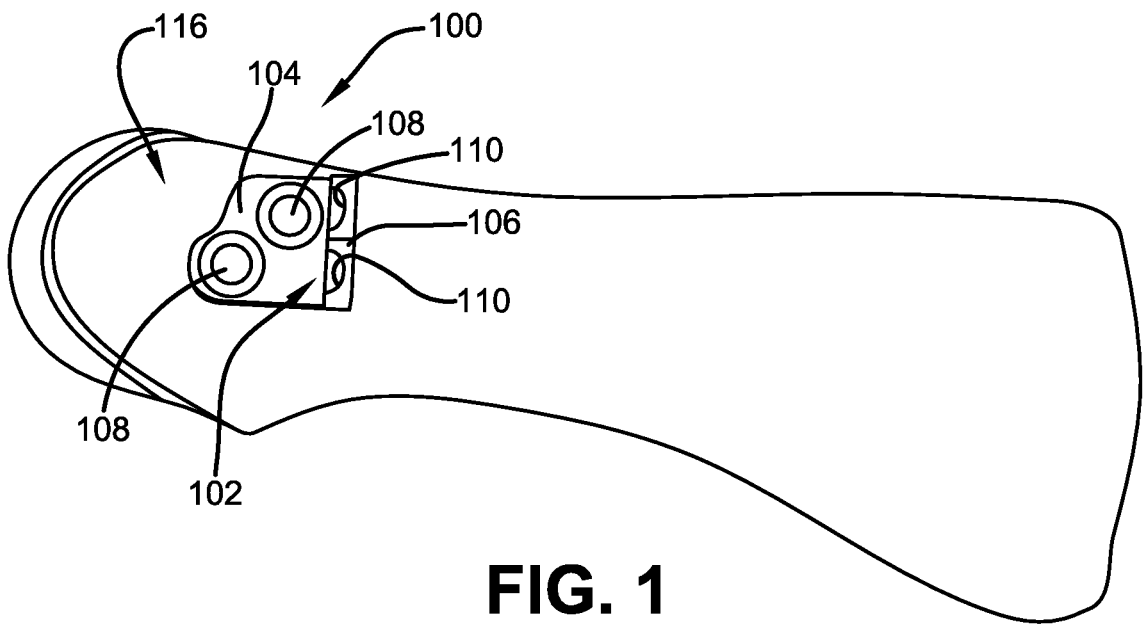
FIG. 1 illustrates a top view of one potential embodiment of the L-plate device of the present invention in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof.

The present invention discloses a base plate having a portion extending from the base plate and used in connection with bunion correction procedures. The plate along with the extension portion secures to a metatarsal head before an osteotomy is performed to allow for greater surgeon control of the metatarsal head during the bunion correction procedure. The L-shaped plate device comprises a shaped body component having two opposing components positioned orthogonally to one another or in an approximately 90 degree angle with a plurality of screw or fasteners openings or apertures positioned on both of the opposing components of the implant.

Bone screws or other fasteners are driven laterally through the apertures of the first opposing component into the metatarsal head. This secures the plate and the extension to the metatarsal head. An osteotomy is performed just proximal to the plate and the metatarsal head is translated to correct the bunion. Bone screws and other fasteners are then placed in the second opposing component apertures and down the metatarsal shaft to fix the correction and provide compression of the osteotomy. Thus, the shaped plate device provides for control and placement of the metatarsal head in the corrected construct during the bunion correction procedure.

Figure 2:
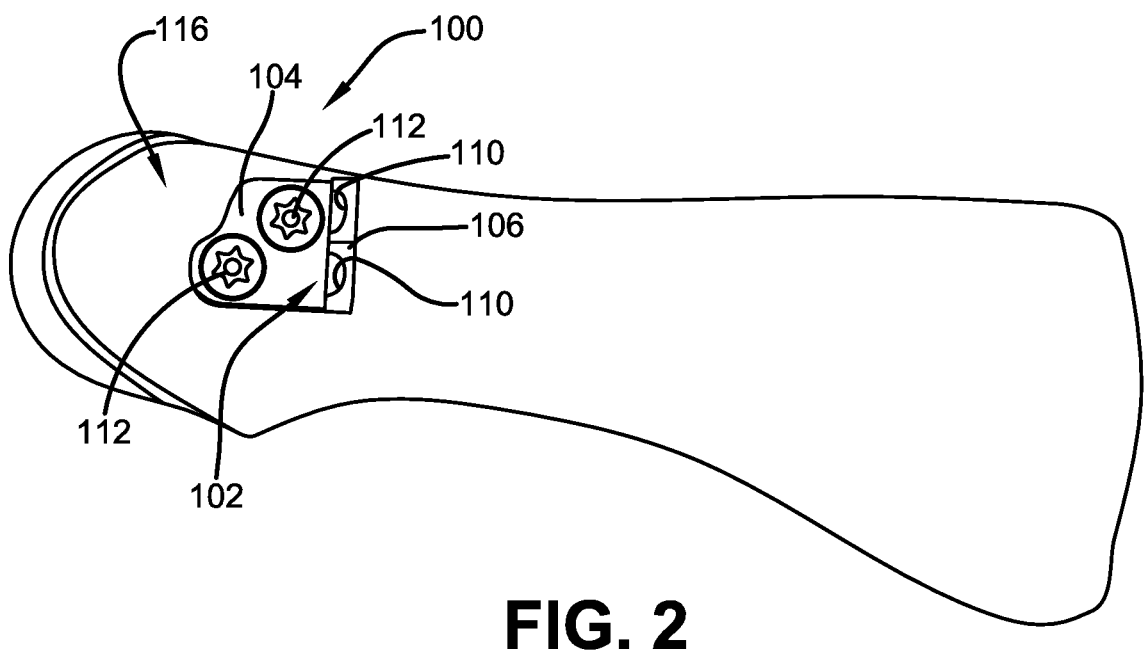
FIG. 2 illustrates a top view of one potential embodiment of the L-plate device of the present invention secured to a metatarsal head via bone screws or other fasteners in accordance with the disclosed architecture.

Referring initially to the drawings, FIGS. 1-2 illustrate one potential embodiment of the shaped plate device 100 which secures to the metatarsal head and allows the surgeon to control the metatarsal head while performing an osteotomy and bunion correction procedure. The plate 100 is a bunion correction device used with open or MIS procedures and includes a body component 102 having a base plate or first portion 104 and a second portion 106 extending from the based plate 104 and the first and second portion disposed in opposing configurations orthogonally to one another or in a range from about 85 to 95 degrees and preferably at an approximately 90 degree angle. The first 104 and second 106 opposing components are formed as one piece and can be positioned together in any suitable angle as is known in the art. Specifically, the angle is typically between 60 and 120 degrees.

Further, the shaped body component 102 can be any suitable size, shape and configuration as is known in the art without affecting the overall concept of the invention. One of ordinary skill in the art will appreciate that the shape and size of the shaped body component 102 as shown in FIGS. 1-2 is for illustrative purposes only and many other shapes and sizes of the shaped body component 102 are well within the scope of the present disclosure. Although dimensions of the L-shaped body component 102 (i.e., length, width, and height) are important design parameters for good performance, the shaped body component 102 with its base plate and extension may be any shape or size that ensures optimal performance during use, and may even be customized to fit the exact specifications/measurements of the patient's first metatarsal.

Figure 3:
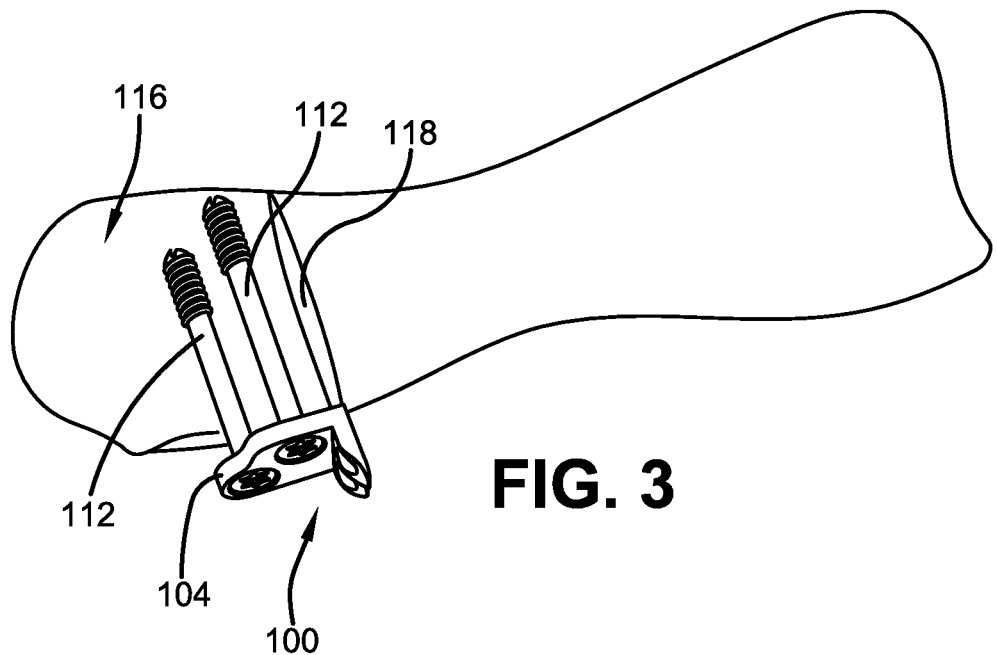
FIG. 3 illustrates a side perspective view of one potential embodiment of the surgical plate of the present invention secured to the metatarsal head in accordance with the disclosed architecture, wherein an osteotomy is performed proximal to the L-plate device.
Figure 4:
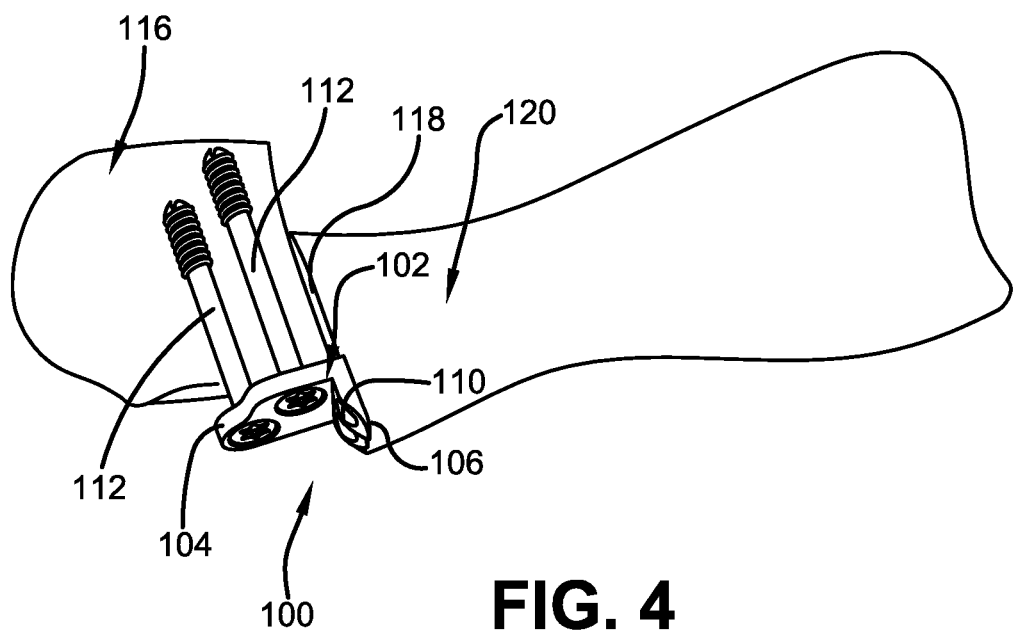
FIG. 4 illustrates a side perspective view of one potential embodiment of the L-shaped plate device of the present invention secured to the metatarsal head in accordance with the disclosed architecture, wherein the metatarsal head is translated to correct the bunion.

Additionally, each of the first 104 and the second 106 opposing components of the plate, include a plurality of apertures or openings 108 and 110 which accept screws or other fasteners 112 and 114 for securing the plate 100 in place. The number of apertures 108 and 110 is typically two, but any suitable number of apertures or openings 108 and 110 can be used depending on the needs and/or preferences of the user. The plurality of apertures 108 and 110 are sized to receive a plurality of bone screws or other fasteners 112 and 114. Specifically, and as best shown in FIGS. 2-4, the first opposing component 104 of the plate 100 includes at least two apertures 108 set apart from one another. The apertures 108 are set apart from one another to allow for more bone area between the screws 112. Bone screws or other fasteners 112 are driven laterally through the apertures or openings 108 to secure the first opposing component 104 to the metatarsal head 116. At least one and preferably two bone screws 112 are inserted through the plurality of apertures 108 positioned in the first opposing component 104 depending on the needs and/or wants of a user. The screws or fasteners may have threading which prevents the screws from moving after insertion.

As best shown in FIGS. 3-4, the osteotomy 118 is performed just proximal to where the plate 100 is secured to the metatarsal head 116. Once the osteotomy 118 is performed, the metatarsal head 116 is translated to correct the bunion. Specifically, the head of the metatarsal 116 is translated laterally in the transverse plane which realigns the MTP joint.

Figure 5:
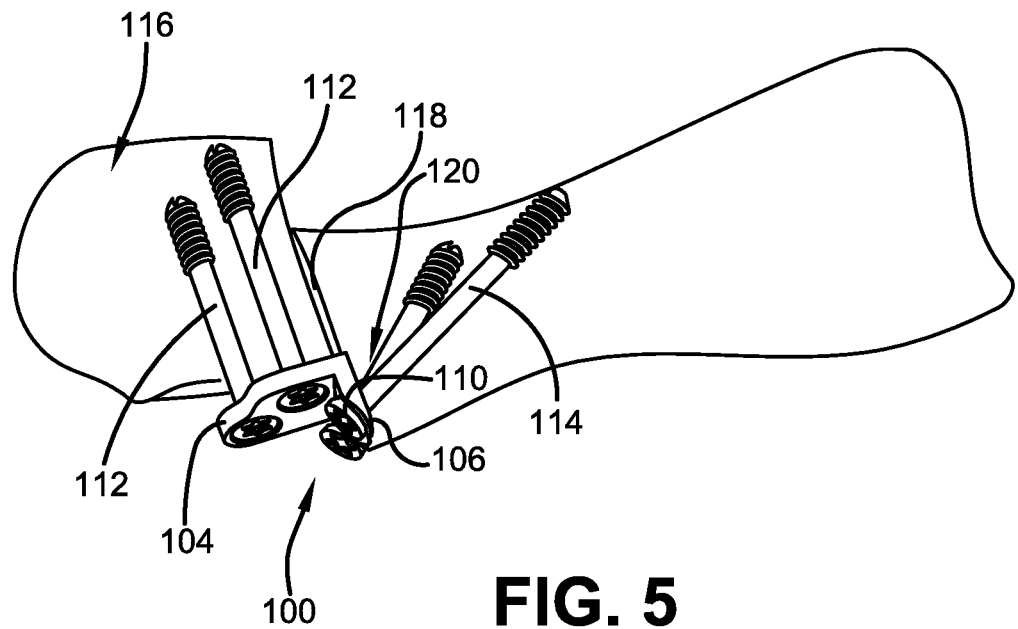
FIG. 5 illustrates a side perspective view of one potential embodiment of the L-shaped plate device of the present invention secured to the metatarsal shaft via bone screws or other fasteners in accordance with the disclosed architecture.
Figure 6:
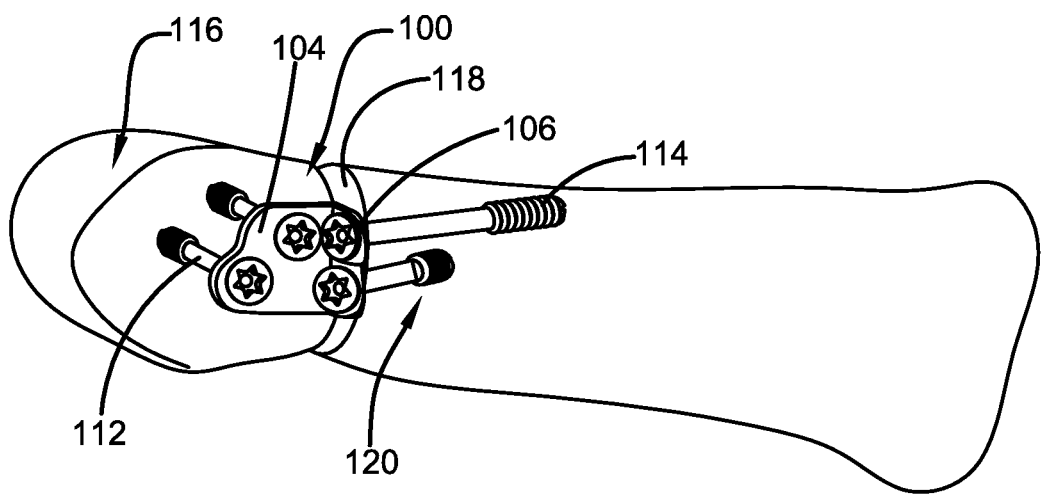
FIG. 6 illustrates a top perspective view of one potential embodiment of the L-shaped plate of the present invention secured to the metatarsal shaft to provide compression of the osteotomy in accordance with the disclosed architecture.

As best shown in FIGS. 5-6, bone screws 114 are then placed in the plate 100 and down the metatarsal shaft 120 to fix the bunion correction and provide compression of the osteotomy 118. Specifically, the second opposing component 106 of the plate 100 has two apertures 110 set in line with one another. These apertures or openings 110 are set in line with one another because there is no cortical bone to engage or risk fracturing. Bone screws or fasteners 114 are driven through the apertures or openings 110 at different angles that do not intersect down the metatarsal shaft 120 to fix the correction and provide compression of the osteotomy. At least one and preferably two bone screws or other fasteners 114 are inserted through the plurality of apertures 110 positioned in the second opposing component 106 depending on the needs and/or wants of a user.

Figure 7:
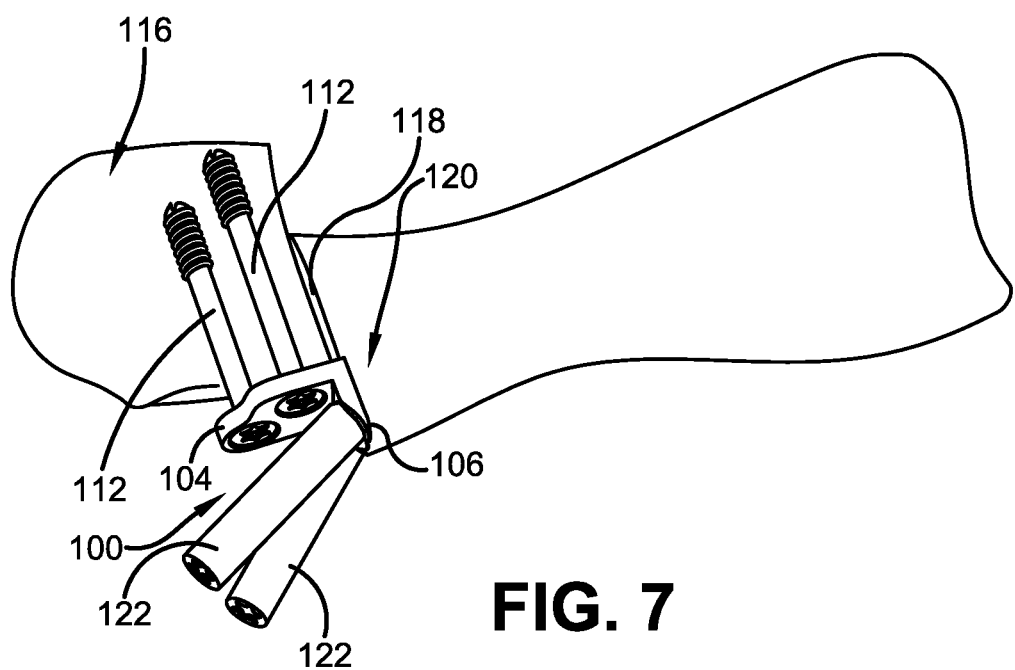
FIG. 7 illustrates a side perspective view of one potential embodiment of the L-shaped plate device having a pair of guide components threaded into the screw or fastener openings or apertures to aid in controlling the metatarsal head and which act as guides to place pins for temporary fixation in accordance with the disclosed architecture.

As best shown in FIG. 7, guide components or handles 122 can be utilized by being removably secured to the plurality of apertures 110 of the second opposing component 106 to aid in controlling the metatarsal head 116. Specifically, a set of guide components 122 are secured to the two apertures 110 of the second opposing component 106 via threading directly into the apertures 110. The set of guide components 122 can be removably secured to the apertures 110 via any other suitable means as is known in the art. The set of guide components 122 are cylindrical in shape and typically cannulated to accept screws, wires and pins for fixation as needed, but can be any suitable shape or size as is known in the art depending on the wants and/or needs of a user. The guide components 122 are used by the surgeon to control the metatarsal head 116, control rotation and allow for easier correction. The guide components 122 can also be used to place pins for temporary fixation if needed.

In a preferred embodiment, the plate 100 is manufactured using additive manufacturing (AM) techniques and grown as one single part. Specifically, the plate 100 is additively printed and able to be manufactured in a variety of sizes as well as to be customizable to fit the exact specifications/measurements of the particular patient. Further, the plate 100 is preferably additively printed with titanium, but can also be additively printed with any other suitable metal or material as is known in the art, as long as the metal or material is medical grade and able to be additively printed. In the alternative, the plate 100 can be manufactured as a machined titanium component. Typically, the plate 100 is machined with titanium, but can be machined with any other suitable metal or material, as long as the metal or material is medical grade and able to be machined. For example, the shaped plate 100 can be manufactured of PEEK, stainless steel or any other biocompatible material.

In operation, as shown in FIGS. 1-6, the shaped plate 100 is applied to the metatarsal head 116 of the foot to correct a bunion deformity. The goal of the surgery is to realign the first metatarsal and the proximal phalanx of the hallux, which restores the distribution of ground reactive forces throughout the human gait cycle and eliminates much of the pain associated with the bunion. Specifically, an incision is made at the dorsal joint surface. The shaped plate 100 is then secured to the metatarsal head 116 via inserting one or more bone screws or fasteners 112 into the apertures or openings 108 of the first portions, base plate or opposing component 104.

An osteotomy 118 is then made in the metatarsal just proximal to the plate 100, which allows the head 116 of the metatarsal to be translated laterally in the transverse plane which realigns the MTP joint. Specifically, a set of guide components 122 are threaded into the apertures 110 of the second portion, extension or opposing component 106 to aid the surgeon in controlling the metatarsal head 116 during translation. The metatarsal head 116 is then translated to correct the bunion.

Pins can be threaded through the set of guide components 122 for temporary fixation, or the set of guide components 122 are removed and bone screws or fasteners 114 are then placed down the metatarsal shaft 120 via inserting the bone screws 114 into the apertures 110 of the second opposing component 106. The bone screws or fasteners 114 act to fix the bunion correction and provide compression of the osteotomy. After implantation of the metallic hardware (i.e., the plate 100 and screws 112 and 114), the surgical site is closed with retained sutures. The foot and lower leg are then typically placed into a splint.

Figure 8:
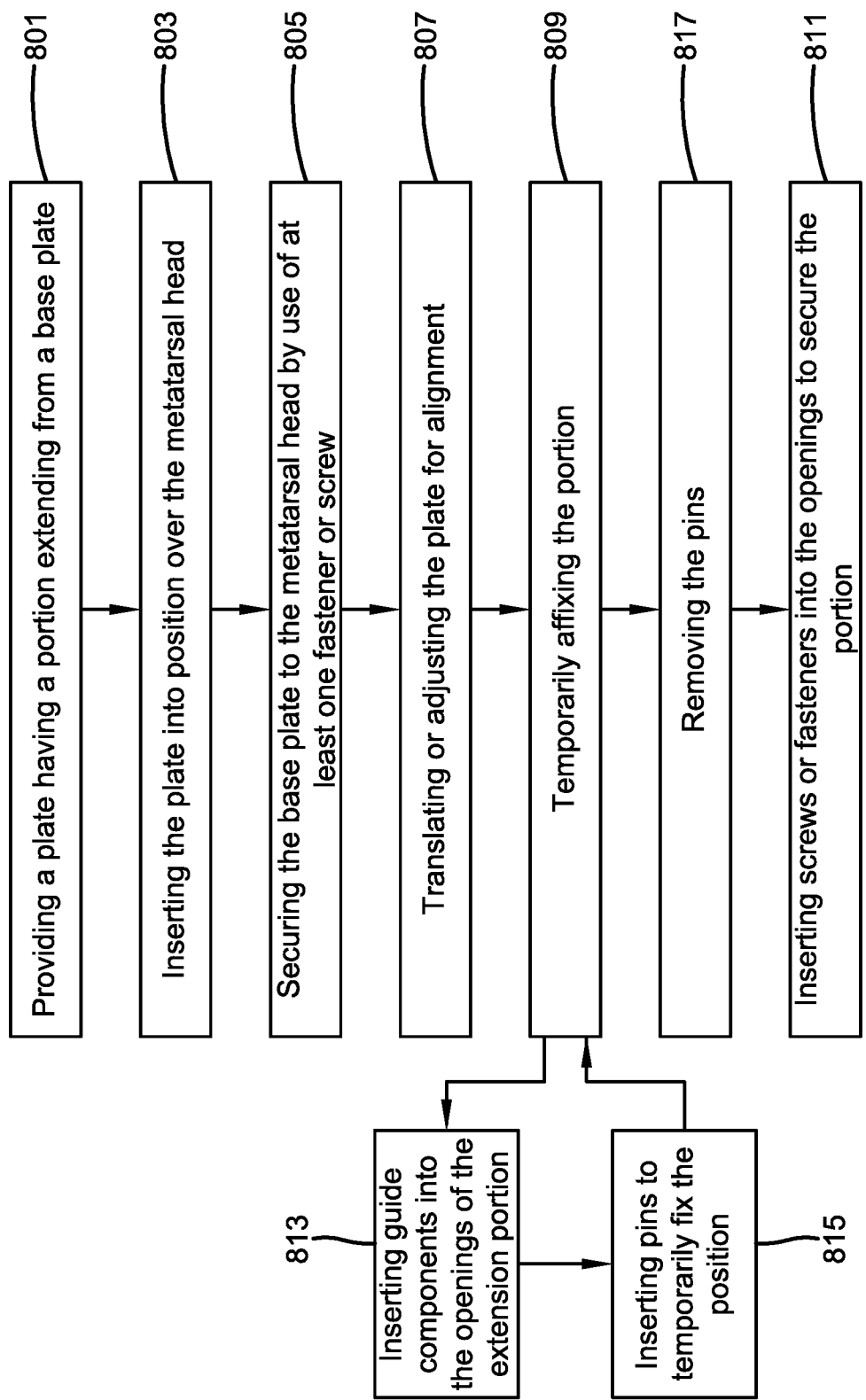
FIG. 8 illustrates a block diagram of one potential and exemplary method of using the L-shaped plate device of the present invention in accordance with the disclosed architecture.

FIG. 8 provides an exemplary method of using the plate of the present invention and starts with first providing a plate having a portion extending off the base plate at step 801 and then inserting the plate over the metatarsal head at step 803. Next, the base plate is secured by used of at least one fastener at step 805. Translating or adjusting the base plate occurs as step 807. At step 809, the portion extending from the base plate is temporarily affixed in position. Step 811 provides for inserting screws into openings into the extension portion. In addition, at step 813 guide components are inserted into openings and pins are inserted into the guide components at step 815. Then at 817 the pins are removed from the guide components.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A plate for a bunion correction comprising:
a base plate comprising a pair of set apart apertures, each set apart aperture configured to accept a fastener; and
a portion extending off the base plate at an angle and comprising a pair of in line apertures, each in line aperture configured to accept a fastener at a different angle from the other in line aperture;
a set of guide components; and
wherein the angle ranges from 60 to 120 degrees; and
wherein each guide component is configured to threadedly engage at least one of the pair of in line apertures in the portion extending off of the base plate and configured to translate a metatarsal head when the base plate is secured to the metatarsal head prior to securing the portion to a metatarsal shaft following an osteotomy performed on the metatarsal head proximal to where the base plate is secured.

2. The plate for bunion correction as recited in claim 1, wherein the angle ranges from 85 to 95 degrees.

3. The plate for bunion correction as recited in claim 1, wherein the angle is 90 degrees.

4. The plate for bunion correction as recited in claim 1, wherein the fastener provides compression to the plate.

5. The plate for bunion correction as recited in claim 1, wherein the base plate and the portion form a generally L-shaped plate.

6. The plate for bunion correction as recited in claim 1, wherein the plate is manufactured from one of a PEEK, a titanium, a stainless steel or a biocompatible material.

7. The plate for bunion correction as recited in claim 1, wherein the plate is manufactured from a titanium using an additive manufacturing technique.

8. An L-shaped plate for use in a podiatry surgery, the L-shaped plate comprising:
a first portion comprising a pair of set apart apertures, each set apart aperture configured to accept a fastener;
a second portion extending outwardly from the first portion at an angle that ranges from between 60 and 120 degrees and comprising a pair of in line apertures; and
a set of guide components threadably attached to the second portion; and
wherein each guide component is canulated and configured to threadedly engage one of the pair of in line apertures in the second portion and configured to rotate a metatarsal head when the first portion is secured to the metatarsal head prior to securing the second portion to a metatarsal shaft following an osteotomy performed on the metatarsal head proximal to where the first portion is secured.

9. The L-shaped plate as recited in claim 8, wherein the angle ranges from between 85 and 95 degrees.

10. The L-shaped plate as recited in claim 8, wherein the angle is 90 degrees.

11. The L-shaped plate as recited in claim 8, wherein each of the first and second portions is manufactured from a select one of a PEEK, a titanium, a stainless steel and a biocompatible material.

12. The L-shaped plate as recited in claim 11, wherein each of the first and second portions is additively manufactured.

13. A method of using a plate for a bunion correction comprising the steps of:
providing the plate, wherein the plate is comprised of a portion extending outwardly from a base plate, and further wherein each of the base plate and the portion are comprised of a pair of openings;
inserting the plate over a metatarsal head;
securing the base plate to the metatarsal head via at least one fastener;
performing an osteotomy on the metatarsal head proximal to where the base plate is secured;
inserting a set of guide components into the pair of openings in the portion extending outwardly from the base plate;
using the set of guide components to align the portion extending outwardly from the base plate with a translated portion of the metatarsal head by translating the metatarsal head laterally in a transverse plane to realign a metatarsophalangeal joint;
inserting a pin into each guide component to temporarily affix the portion extending from the base plate to the translated portion of the metatarsal head; and
removing each pin and permanently fixing the portion extending from the base plate to the translated portion of the metatarsal head via a pair of fasteners inserted at different angles into a metatarsal shaft proximal to the osteotomy.

* * * * *